United States Patent
Mannarini

(10) Patent No.: US 8,198,321 B2
(45) Date of Patent: Jun. 12, 2012

(54) ANTI-MICROORGANISM TERPENIC COMPOSITION

(75) Inventor: Aurèle Henri Mannarini, Conca (FR)

(73) Assignees: Bernard Lucien Gombert (FR); Aurele Henri Mannarini (FR)

( * ) Notice: Subject to any disclaimer, the term of this patent is extended or adjusted under 35 U.S.C. 154(b) by 365 days.

(21) Appl. No.: 12/515,057

(22) PCT Filed: Nov. 16, 2007

(86) PCT No.: PCT/FR2007/001895
§ 371 (c)(1),
(2), (4) Date: Jun. 18, 2009

(87) PCT Pub. No.: WO2008/068427
PCT Pub. Date: Jun. 12, 2008

(65) Prior Publication Data
US 2010/0286413 A1    Nov. 11, 2010

(30) Foreign Application Priority Data
Nov. 17, 2006 (FR) .................................. 06 10073

(51) Int. Cl.
*A61K 31/34* (2006.01)
*A61K 31/315* (2006.01)
*C07D 307/62* (2006.01)
*C07F 3/06* (2006.01)

(52) U.S. Cl. ........ 514/474; 514/494; 549/315; 549/317; 556/132

(58) Field of Classification Search ................ 514/474, 514/494; 549/315, 317; 556/132
See application file for complete search history.

(56) References Cited

FOREIGN PATENT DOCUMENTS

| | | |
|---|---|---|
| DE | 26 30 169 A1 | 10/1977 |
| DE | 38 01 900 A1 | 9/1989 |
| FR | 2 303 537 A1 | 10/1976 |
| GB | 266 727 A | 9/1927 |
| GB | 753 742 A | 8/1956 |
| GB | 2 225 013 A | 5/1990 |

OTHER PUBLICATIONS

International Search Report dated May 28, 2008, issued in corresponding international application No. PCT/FR2007/001895.

*Primary Examiner* — Bernard Dentz
(74) *Attorney, Agent, or Firm* — Ostrolenk Faber LLP

(57) ABSTRACT

The invention relates to a terpenic composition for use as an anti-micro-organism or anti-viral agent comprising a cyclic terpenic compound obtained from a terpene of the general formula $(C_5H_8)_n$, n being in the range of 2 to 5; and to a vector-forming organic substance, associated to the said cyclic terpenic compound.

9 Claims, No Drawings

ANTI-MICROORGANISM TERPENIC COMPOSITION

CROSS REFERENCE TO RELATED APPLICATIONS

The present application is a 35 U.S.C. §371 National Phase conversion of PCT/FR2007/001895, filed Nov. 16, 2007, which claims benefit of French Application No. 0610073, filed Nov. 17, 2006, the disclosure of which is incorporated herein by reference. The PCT International Application was published in the French language.

BACKGROUND OF THE INVENTION

The present invention relates to an anti-microorganism terpenic composition and to the use thereof, in particular against HIV.

Terpenes, and in particular camphor and its derivatives, have been widely used in medicine and they were reputed to be active against all illnesses. Camphor was generally used by local external application as an antiseptic or an anesthetic. Camphor is also used internally as a cardiotonic. However, it is barely water-soluble, which limits its use.

Camphor is generally obtained from the alpha-pinene contained in oil of turpentine, which is obtained from the resinous sap that flows from maritime pine. Thus, alpha-pinene is converted to camphor while going through various intermediates, and in particular bornyl chloride, camphene and the organic ester of isoborneol.

Moreover, camphor substitution derivatives combined with mercury have also been widely used in the past as diuretics.

However, given their low water-solubility, the use of terpenes, and in particular derivatives of camphor or its synthetic intermediates, remains limited in human and animal medicine.

In addition, a certain number of its derivatives are found to be cytotoxic, and in particular the ketone derivatives.

However, terpene chemistry has been around for a long time and is now well known and, consequently, the costs for obtaining these biologically active molecules with therapeutic virtues are relatively low.

Thus, one problem which arises and which the present invention intends to solve is that of providing a terpenic composition that can be used as an anti-microorganism agent and that can easily be administered to humans. Another objective is to provide a terpenic composition for which the effectiveness of the active ingredient is improved.

SUMMARY OF THE INVENTION

With the objective of solving this problem, the present invention proposes, according to a first aspect, a terpenic composition for use as an anti-microorganism agent. According to the invention, the terpenic composition comprises: a cyclic terpenic compound obtained from a terpene of general formula $(C_5H_8)_n$, n being in the range of 2 to 5; and a vector-forming organic substance, associated with said cyclic terpenic compound, and said cyclic terpenic compound associated with said organic substance is bonded to a metal cation.

Thus, one characteristic of the invention lies in the association of a cyclic terpenic compound which has anti-microorganism properties, with an organic substance for conveying the active terpenic compound to the microorganisms, said cyclic terpenic compound associated with said organic substance being bonded to a metal cation which then promotes the anti-microorganism properties of said composition. In addition, the organic substance optionally makes it possible to transfer the terpenic compound through the microorganism itself, so as to reach a given target, for example its genetic material, where the terpenic compound can bring about inhibition thereof.

Advantageously, the cyclic terpenic compound is obtained from a monoterpene, for which n=2, and the anti-microorganism activity of which is greater than that of the other terpenes. Preferably, the monoterpene results in a terpenic compound having a single ring containing five carbon atoms.

For example, the terpenic compound is obtained by oxidation of camphor, itself derived from the conversion of alpha-pinene as indicated above.

Camphene, which is an isomer of pinene, and in particular its acid derivatives and alcohol derivatives such as the camphols: borneol, camphoric acid, camphoric hydroxide or else camphor diol, are entirely suitable terpenic compounds. They are obtained by synthesis, from camphene. An acid-alcohol is obtained, by virtue of a peracid, by means of the Baeyer-Villiger reaction, or alternatively, an aldehyde is obtained by treatment with potassium hydroxide.

According to one particularly advantageous embodiment of the invention, the terpenic compound has at least one carboxylic acid function, and preferably two. In addition, said terpenic compound forms ester bonds with said organic substance. Advantageously, the terpenic compound is camphoric acid.

In addition, the metal cation associated with the terpenic compound is chosen from the metals of the third and fourth periods of elements of Mendeleev's Periodic Table of Elements, also called Periodic Classification of Elements. Preferably, the metal cation is chosen from the elements of the collection comprising zinc, copper, nickel and magnesium, or alternatively manganese.

However, other metals of the fifth and sixth periods of the abovementioned periodic table, such as tin or mercury, can also form a stable compound.

Furthermore, the vector-forming organic substance which makes it possible to convey the terpenic compound through the tissues and to take it to its potential target, the microorganism to be inactivated, is chosen from carbohydrates, preferably monosaccharides and osides, and in particular gluconates, amino acid compounds, vitamins, nucleic acids or else benzene compounds. Salicylic acid or para-aminosalicylic acid and cinnamic acid are in particular included in these benzene compounds.

Among the vitamins, folic acid, para-aminobenzoic acid or else ascorbic acid will in particular be selected. Zinc ascorbo-camphorate or zinc bornyl folate or else manganese bornyl gluconate, for example, will thus be formed. The use of acetic acid is also envisioned so as to form zinc aceto-camphorate. The metal ion of one or other of the abovementioned compounds may be replaced with one or other of the metal ions mentioned above, zinc or manganese.

According to another aspect, the invention proposes the use of a terpenic composition as described above, for preparing a medicament for use in conquering HIV or else as an antimicrobial agent for external use. Thus, such a medicament is capable of being produced at a very advantageous cost, since the above-mentioned terpenic composition can itself be produced at low cost.

The terpenic composition for the purpose of preparing a medicament can be diluted in an aqueous solution or in a water/alcohol mixture and can be conditioned with a physiologically acceptable excipient, in the form of a gel for external application or in the form of an injectable solution. However, the terpenic composition is also able to be conditioned as a powder so that it can be administered orally.

In general, the abovementioned terpenic composition can be used for the preparation of antiseptic, microbicidal or disinfectant agents, whether for the treatment of human and animal or plant pathologies or alternatively in health applications.

According to another aspect, the invention relates to a method for preparing a terpenic composition, according to which a vector-forming organic substance is associated with a cyclic terpenic compound obtained from a terpene of general formula $(C_5H_8)_n$, n being in the range of 2 to 5, and said cyclic terpenic compound being bonded to a metal cation.

According to yet another aspect, the invention relates to the use of a terpenic compound as described above, for obtaining a medicament for combating a viral or retroviral infection, for example of the HIV type.

Other particularities and advantages of the invention will emerge on reading the description, provided hereinafter, of specific embodiments of the invention, given by way of non-limiting indication.

One particularity of the invention lies in the use of a cyclic terpenic compound derived from a terpene of general formula $(C_5H_8)_n$, where n is in the range of 2 to 5, with a metal cation and a vector-forming organic substance.

EXAMPLES

In the examples below, the terpenic compositions according to the invention were prepared proportionally with experimental amounts which make it possible to show their effects and their effectiveness. However, extrapolation of these experimental amounts to industrial amounts does not raise any difficulty.

Example 1

A first preparation based on ascorbic acid, camphoric acid and zinc was prepared under ambient temperature and pressure conditions, i.e. approximately 298.15 K and $10^5$ Pa. Nevertheless, in certain phases, the mixtures are slightly heated and stirred.

According to this first example, the camphoric acid of formula (I):

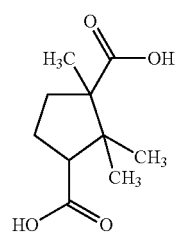

is prepared from the camphor obtained according to a well-known method using pinene as starting material, by oxidation of the camphor.

Thus, 200 mg of camphoric acid are solubilized in 1 g of 90° ethanol. Next, 0.5 g of ultrapure water is added to the mixture.

The camphoric acid mixture is then combined with a zinc oxide in solution. For this, 81.3 mg of zinc oxide are mixed with 1 g of ultrapure water, and this mixture, after stirring, forms a milky solution. The abovementioned camphoric acid mixture is slowly poured into the milky solution. The whole is stirred moderately and intermittently. In addition, between each stirring phase, it is slightly heated, for example in an oven, in order to accelerate the reaction.

A precipitate, zinc camphorate, then forms and is recovered by extraction of the solvent, either by heating or by freeze-drying.

Next, 265.3 mg of zinc camphorate thus obtained are mixed with a solution of 10 g of pure water containing 176 mg of ascorbic acid of formula II:

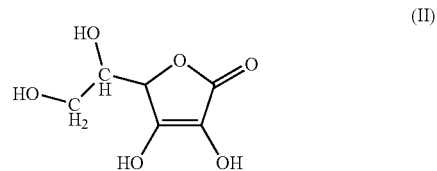

Preferably, the mixing is carried out at a temperature below 298.15 K. The preparation thus obtained is moderately stirred and is kept in the dark in order to prevent oxidation of the ascorbic acid.

During the stirring, the zinc camphorate dissolves so as to then form zinc ascorbo-camphorate in solution. However, only ¼ of the zinc camphorate of the preparation dissolves, while the remaining ¾ of the zinc camphorate stays undissolved in the mixture. On the other hand, all the ascorbic acid disappears and thus reacts with the zinc camphorate. This preparation, which is then diluted to 1/200, or to 1/200th, consequently includes molecular compounds comprising ¼ mol of zinc ascorbo-camphorate molecules, and in the case in point ¼ of 1/1000 mol of molecules, per ¾ mol of zinc camphorate molecules, and in the case in point per ¼ of 1/1000 mol of molecules.

As will be explained hereinafter, this powder in solution makes it possible to prepare a terpenic composition for inactivating microorganisms and viruses, in particular HIV.

A second preparation is carried out according to example 2, with the same basic products, zinc camphorate and ascorbic acid, and according to the same protocol, except for the amount of ascorbic acid. Specifically, in this example, 352 mg of ascorbic acid are dissolved in 10 g of ultrapure water with the zinc camphorate. Thus, the second composition comprises not one, but two mol of ascorbic acid per mole of camphoric acid. On the other hand, according to this second preparation, it is now ½, half, the zinc camphorate which dissolves, while the ascorbic acid reacts completely. Consequently, the preparation includes molecular compounds comprising mol of zinc ascorbo-camphorate molecules per mol of zinc camphorate molecules.

A third preparation is carried out according to example 3, also with the same basic products and according to the same protocol, except for the amount of ascorbic acid, which is then 704 mg. The third composition then comprises four mol of ascorbic acid per mole of camphoric acid. In addition, according to this third preparation, all the zinc camphorate dissolves and reacts with the ascorbic acid. Thus, it is concluded therefrom that four mol of ascorbic acid react with one mol of zinc camphorate, hence it will be deduced that four molecules of ascorbic acid attach to one molecule of zinc camphorate; and the molecule thus formed can be written: $Zn[(C_{10}H_{14}O_4)(C_6H_4O_6)_4]$. This molecule can also form a certain number of hydrates which have not been described herein.

It will be observed that the dissolved zinc ascorbo-camphorate can be recovered in the form of a powder by freeze-drying.

Moreover, a fourth preparation, according to example 4, is prepared, no longer with ascorbic acid, but using cinnamic acid of formula:

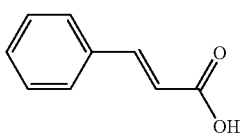

(III)

Example 4

148 mg of cinnamic acid are solubilized in 1 g of ethanol and 500 mg of ultrapure water are added thereto. 132.65 mg of zinc camphorate obtained according to the above method are incorporated into the solution thus prepared. After dissolution, a precipitate forms, said precipitate corresponding to zinc cinnamo-camphorate, which is water-soluble at 1/1000, denoted 1/1000th dilution (one part by weight per 1000 parts of water by weight), which is recovered.

Thus, table I below summarizes the molar proportions of the basic constituents of the four preparations above, obtained in the corresponding four examples and on the basis of which terpenic compositions in accordance with the invention are prepared.

TABLE I

| Preparations | Camphoric acid | Ascorbic acid | Cinnamic acid | Zinc oxide ZnO |
|---|---|---|---|---|
| First | 200 mg | 176 mg | | 81.3 mg |
| Second | 200 mg | 352 mg | | 81.3 mg |
| Third | 200 mg | 704 mg | | 81.3 mg |
| Fourth | 100 mg | | 148 mg | 40.65 mg |

In order to carry out cytotoxicity and infection-inhibiting activity tests, three cell types and two viral strains were used. This involved a laboratory strain HIV-1$_{NDK}$(X4-tropic) which was amplified by lymphocytes originating from healthy donors, and a primary strain HIV-1$_{Bal}$ (R5-tropic) which was amplified by macrophages.

As regards the cell types, macrophages and dendritic cells were obtained from peripheral blood mononuclear cells. In addition, lymphocytes were provided.

The cytotoxicity of the terpenic compositions is verified using the MTT test from the company Sigma. The abovementioned macrophages or dendritic cells are thus cultured and then treated with each of the compositions, and the MTT reagent is then added. The latter then forms crystals with the highly metabolic live cells. The absorbance at 490 nm of the dissolved crystals then corresponds to the number of live cells. Thus, by comparison with cultured but nontreated macrophages and dendritic cells, a percentage survival is obtained, revealing the toxicity of the terpenic compositions.

The results show that the dilutions to 1/10 000, denoted 1/10 000th, to 1/500th and to 1/100th of the abovementioned four compounds, are not toxic to the cells studied.

As regards the inhibitory activity, the macrophages or the dendritic cells are incubated with viral particles of the above-mentioned strains, HIV-1$_{NDK}$(X4-tropic) or HIV-1$_{Bal}$ (R5-tropic), in the presence and absence of the terpenic compositions. The cells are subsequently washed and then put back in culture and, finally, centrifuged. The supernatants are then recovered and the viral particles are lyzed in order to measure the concentration of a viral protein using the ELISA assay. In this way, the inhibitory activity of the terpenic compositions is evaluated by comparison between the nontreated infected cells and the treated infected cells.

In addition, tests for transfer of the virus, from the dendritic cells to autologous T lymphocytes, i.e. T lymphocytes originating from the same stem cells, were carried out.

For this, dendritic cells are transferred and incubated with each of the terpenic compositions and the virus. Next, after washing, autologous T lymphocytes are added in a ratio of one dendritic cell to five T lymphocytes. The concentration of viral proteins of the abovementioned type is then evaluated by means of the ELISA assay.

Next, the inhibition of the infection of the macrophages was evaluated. Since the latter are potential reservoirs for HIV, it is a question of measuring the ability of the terpenic composition to prevent infection of the macrophages.

TABLE II

Test for inhibition of macrophage infection

| Dilution | HIV-1$_{NDK}$ (X4-tropic) | HIV-1$_{Bal}$ (R5-tropic) |
|---|---|---|
| First to 1/200th | 56.9 +/− 5% | 48.1 +/− 4% |
| Second to 1/200th | 61.5 +/− 3% | 58.5 +/− 4% |
| Third to 1/200th | >95% | >95% |
| Fourth to 1/2000th | >90% | >90% |

It is found here that the terpenic composition obtained from the third preparation, and diluted to 1/200, denoted 1/200 th, inhibits by more than 95% the infection of the macrophages with strains of the X4-tropic and R5-tropic group. Moreover, for the third and fourth compositions obtained, respectively, from the third and fourth preparations, the latter being diluted no longer to 1/200th, but to 1/2000th, the same results are obtained.

Furthermore, tests were carried out on the inhibition of dendritic cell infection, since these cells are involved in HIV transmission at the mucosal level.

TABLE III

Test for inhibition of dendritic cell infection

| Dilution | HIV-1$_{NDK}$ (X4-tropic) | HIV-1$_{Bal}$ (R5-tropic) |
|---|---|---|
| First to 1/200th | 32.4 +/− 3% | 75.7 +/− 5% |
| Second to 1/200th | 31.5 +/− 2% | 73.4 +/− 1% |
| Third to 1/200th | >95% | >95% |
| Fourth to 1/2000th | 0% | 0% |

Here again, the terpenic composition obtained from the third compound, and diluted to 1/200th, inhibits by more than 95% the infection of the dendritic cells with the X4 and R5 strains. It will be noted here that the third composition obtained from the third preparation and diluted to 1/2000th also makes it possible to obtain the same results. Thus, diluted to 1/100th, this same third preparation is capable of rendering the X4 strains noninfectious.

Dendritic cells express, at their surface, an adhesion protein, DC-SIGN, which forms a viral receptor capable of capturing HIV and of facilitating the infection of permissive cells via a "trans-infection" mechanism. This is because the DC- SIGN receptor can interact with the envelope of HIV and hold the virion in an infectious state so as to subsequently transmit it to permissive T lymphocytes in the adjacent lymph nodes.

TABLE IV

Test for inhibition of transfer from dendritic cells to T lymphocytes

| Dilution | HIV-1$_{NDK}$ (X4-tropic) | HIV-1$_{Bal}$ (R5-tropic) |
|---|---|---|
| First to 1/200th | 83.1 +/− 3% | 82.3 +/− 7% |
| Second to 1/200th | 65.4 +/− 3% | 81.3 +/− 5% |
| Third to 1/200th | >95% | >95% |
| Fourth to 1/2000th | 0% | 0% |

Thus, a 1/200th dilution of the terpenic composition originating from the third compound then causes a more than 95% inhibition of infection of the dendritic cells with the R5-tropic and X4-tropic strains. Here again, the third composition obtained from the third preparation and diluted to 1/2000 th gives the same results.

Moreover, another terpenic composition, in accordance with the invention, zinc aceto-salicylo-borneolate, was prepared in an organic solution. This fifth preparation, diluted to 50%, was tested in macrophage infection inhibition, and it inhibits by more than 50% the infection of macrophages with strains of the R5-tropic group. It is thus shown that other organic substances, and in the case in point, according to this fifth preparation, acetic acid and salicylic acid, can be used to form a vector.

Consequently, terpenic compositions prepared based on the abovementioned compositions make it possible to prepare medicaments for internal or external use for combating HIV. It will be noted that the terpenic composition which is the most effective and which has the greatest activity in all the abovementioned tests is the composition resulting from the third preparation. Thus, the role of ascorbic acid as a vector is determining.

It will also be noted that this terpenic composition resulting from the third preparation has a detergent activity with respect to the X4 strains, when it is diluted to 1/100th.

As regards external applications, the terpenic compositions are formulated with a physiologically acceptable excipient in the form of a gel or of an ointment.

Thus, in order to use the terpenic composition resulting from the third preparation in a microbicidal preparation with a view to combating HIV, vaginal toxicity tests were carried out on the rabbit model.

The white New Zealand rabbit model was used to show whether repeated applications of the terpenic composition resulting from the third preparation resulted in vaginal irritations. For this, the animals were treated with doses of 1 ml of 2 compositions, one containing 2.1 µg/milliliter of the composition and the other 4200 µg/milliliter. Control animals were treated only with a PBS buffer under the same conditions.

All the animals, 9 in total, received daily intravaginal doses of the abovementioned compositions for 10 consecutive days. 24 hours after the final application of compositions, the vaginal tract of all the animals was excised and a histopathological evaluation was carried out. As was expected, the control animals treated with the PBS buffer exhibited normal tissues. The vaginal tissues of the other two groups of animals, treated with the two compositions with a different dilution, exhibited infiltrations of cells with polymorphic nuclei in the epithelial and subepithelial connective tissues. However, the infiltration observed and the vascular congestion were considered to be "minimal" and no edema was observed. The vaginal epithelium remained entirely intact and only minor morphological modifications were noted.

Thus, the composition according to the above-mentioned two dilutions brought about only a "minimal" vaginal irritation. Thus, this degree of irritation is acceptable for vaginal use. Consequently, these tests made it possible to verify the innocuousness of the composition.

Thus, the tests show that the terpenic derivatives have a high antiretroviral activity and are capable of inhibiting viral replication within the mucosal target cells, such as macrophages, dendritic cells and lymphocytes. Some of them effectively inhibit HIV transfer from dendritic cells to CD4 T lymphocytes, which is one of the major hypothetical mechanisms involved in the virus crossing the mucous membranes and in the amplification of its dissemination within the mucous membranes.

Since the terpenic derivatives constitute a class of antiretroviral compounds distinct from those which already exist and since they inhibit the entry and the replication of HIV-1 via hitherto unpublished mechanisms, these compounds become sources of antiviral molecules that are attractive from both a preventive and therapeutic point of view.

For internal applications, the terpenic compositions are obtained in solid form, for example pulverulent form, and can subsequently be converted into tablets for oral administration or solubilized in a physiologically acceptable excipient so as to be administered parenterally.

Moreover, the terpenic compositions were tested in toxicological terms in mice and revealed an LD 50 (lethal dose starting from which 50% of individuals die), at 48 hours after administration, of 5.5 g plus or minus 0.5 g per kilogram. Thus, such compositions are considered to be atoxic.

Furthermore, the subacute toxicity tests also showed that the terpenic compositions according to the invention were suitable for treatments for human pathologies.

In human therapy, the above terpenic compositions are formulated in a proportion of 1 to 300 mg per absorption for fractional or nonfractional intakes, for a dosage ranging from 1 to 3000 mg per day in adults.

Of course, the dosages could be higher if other embodiments of the invention were used, and in particular if the terpenic compound resulted from the bornyl.

What is claimed is:

1. A terpenic composition for use as an anti-microorganism or antiviral agent, wherein the composition comprises:
   camphoric acid as a cyclic terpenic compound obtained from a terpene of general formula $(C_5H_8)_2$; and
   ascorbic acid as a vector-forming organic substance, associated with said cyclic terpenic compound; and
   wherein said cyclic terpenic compound associated with said organic substance is bonded to a metal cation.

2. A terpenic composition for use as an anti-microorganism or antiviral agent, wherein the composition comprises:
   camphoric acid as a cyclic terpenic compound obtained from a terpene of general formula $(C5H8)_2$; and
   cinnamic acid as a vector-forming organic substance, associated with said cyclic terpenic compound; and
   wherein said cyclic terpenic compound associated with said organic substance is bonded to a metal cation.

3. The terpenic composition as claimed in claim 1, wherein said terpenic compound forms ester bonds with said organic substance.

4. The terpenic composition as claimed in claim 2, wherein said terpenic compound forms ester bonds with said organic substance.

5. The terpenic composition as claimed in claim 1, wherein said metal cation is chosen from the metals of the third and fourth periods of elements of the Periodic Table of Elements.

6. The terpenic composition as claimed in claim 2, wherein said metal cation is chosen from the metals of the third and fourth periods of elements of the Periodic Table of Elements.

7. The terpenic composition as claimed in claim 6, wherein said metal cation is chosen from the elements of the collection comprising zinc, copper, manganese and magnesium.

8. A method for producing a terpenic composition as claimed in claim 1 wherein ascorbic acid is associated with camphoric acid, said camphoric acid being bonded to a metal cation.

9. A method for producing a terpenic composition as claimed in claim 2 wherein cinnamic acid is associated with camphoric acid, said camphoric acid being bonded to a metal cation.

* * * * *